United States Patent
Jensen et al.

(10) Patent No.: US 10,251,406 B2
(45) Date of Patent: Apr. 9, 2019

(54) DEVICE FOR LOOSENING BONES FROM A MEAT PIECE SUCH AS RIBS FROM A BELLY PIECE OF SLAUGHTERED ANIMAL

(71) Applicant: Teknologisk Institut, Taastrup (DK)

(72) Inventors: Carsten Jensen, Taastrup (DK); Bjarne Vestergaard-Jensen, Taastrup (DK); Kim Blichfeldt Kirkeby, Taastrup (DK); Max Pedersen, Taastrup (DK); Flemming Christensen, Taastrup (DK); Mikkel Engbo Jørgensen, Taastrup (DK); Simon Kyhn Stenfeldt, Taastrup (DK)

(73) Assignee: Teknologist Institut, Taastrup (DK)

( * ) Notice: Subject to any disclaimer, the term of this patent is extended or adjusted under 35 U.S.C. 154(b) by 0 days.

(21) Appl. No.: 16/068,495

(22) PCT Filed: Jan. 9, 2017

(86) PCT No.: PCT/EP2017/050318
§ 371 (c)(1),
(2) Date: Jul. 6, 2018

(87) PCT Pub. No.: WO2017/118756
PCT Pub. Date: Jul. 13, 2017

(65) Prior Publication Data
US 2019/0008172 A1    Jan. 10, 2019

(30) Foreign Application Priority Data

Jan. 8, 2016  (DK) .................................. 2016 00010
May 2, 2016  (DK) .................................. 2016 00265
May 2, 2016  (DK) .................................. 2016 00266

(51) Int. Cl.
*A22C 17/00*  (2006.01)
*B25J 11/00*  (2006.01)
(Continued)

(52) U.S. Cl.
CPC ........ *A22C 17/0046* (2013.01); *A22C 17/004* (2013.01); *B25J 9/1679* (2013.01);
(Continued)

(58) Field of Classification Search
CPC ...... A22C 17/00; A22C 17/004; A22C 17/046
(Continued)

(56) References Cited

U.S. PATENT DOCUMENTS 4,422,216 A    12/1983  Spotzl
6,306,028 B1 *  10/2001  White ................. A22B 5/0017
                                                     452/125
(Continued)

FOREIGN PATENT DOCUMENTS

CH    592 417 A5    10/1977
CH    597 762 A5    4/1978
(Continued)

*Primary Examiner* — Richard T Price, Jr.
(74) *Attorney, Agent, or Firm* — Holland & Hart LLP

(57) ABSTRACT

Disclosed is a device for loosening bones such as ribs from a meat piece from slaughtered animals such as pigs. The bone puller such as rib puller can be hand-held and e.g. pneumatic activated or connected to a robot, and is much easier to use than prior art pneumatic rib pullers and also impose less working stress upon the user. The bone puller may comprise a counter hold for supporting the device towards a belly piece from a slaughtered animal, a string for loosening a bone, a movable pull bar for pulling the string, and a holding-down bar for holding down a bone while loosening this bone. The device may further comprise loading means located at the end of the holding-down bar such that the string can surround the loading means and where this loading means secure feeding of the string around an exposed bone end before loosening this bone.

15 Claims, 5 Drawing Sheets

(51) Int. Cl.
  *G01N 21/47* (2006.01)
  *G01N 21/94* (2006.01)
  *G01N 21/49* (2006.01)
  *G01N 33/12* (2006.01)
  *B25J 9/16* (2006.01)

(52) U.S. Cl.
  CPC ........ *B25J 11/005* (2013.01); *G01N 21/4795* (2013.01); *G01N 21/49* (2013.01); *G01N 21/94* (2013.01); *G01N 33/12* (2013.01)

(58) Field of Classification Search
  USPC ................ 452/125, 128, 135, 149–153, 160
  See application file for complete search history.

(56) References Cited

U.S. PATENT DOCUMENTS

| | | | | |
|---|---|---|---|---|
| 7,252,583 B1* | 8/2007 | Jones | .................... | A22B 5/0005 452/102 |
| 8,342,917 B2* | 1/2013 | Byrd | .................... | A22C 25/025 452/105 |
| 8,808,069 B2* | 8/2014 | Schot | ................. | A22C 21/0076 452/136 |
| 2002/0067797 A1 | 6/2002 | Safai et al. | | |
| 2003/0098796 A1 | 5/2003 | Bond et al. | | |
| 2005/0085176 A1 | 4/2005 | Houtz | | |
| 2011/0195647 A1 | 8/2011 | Schill et al. | | |

FOREIGN PATENT DOCUMENTS

| | | |
|---|---|---|
| CH | 604 536 A5 | 9/1978 |
| DE | 25 10 956 A1 | 9/1976 |
| DE | 28 18 722 A1 | 11/1979 |
| DE | 20 2007 014734 U1 | 12/2007 |
| DE | 20 2007 014 734 U1 | 1/2008 |
| EP | 0 469 680 A1 | 2/1992 |
| EP | 0 502 581 A1 | 9/1992 |
| GB | 2 150 416 A | 7/1985 |
| GB | 2 446 822 A | 8/2008 |
| JP | 2014007982 A | 1/2014 |
| WO | WO 2011/113081 A1 | 9/2011 |

* cited by examiner

DEVICE FOR LOOSENING BONES FROM A MEAT PIECE SUCH AS RIBS FROM A BELLY PIECE OF SLAUGHTERED ANIMAL

The present invention relates to a device for loosening bones from a meat piece such as loosening ribs from a belly piece of a slaughtered animal. Such a device is commonly denoted a rib puller when used to loosen ribs. An improved hand held tool for removal of bones such as ribs as well as a tool for automatic removal of bones such as ribs are described. A measuring system for determining the presence and location of bones in meat pieces such as bones located near the edge of a meat piece is also described and may be part of an automatic system for removing bones.

BACKGROUND OF INVENTION

After slaughtering of pigs the ribs may be removed from the belly either as different kinds of spareribs where the meat between the ribs are removed together with the ribs or the ribs can be removed from the belly piece removing only as little meat as possible between the ribs i.e. removing all the ribs as single ribs and leaving as much meat at the belly piece as possible.

At many pig abattoirs single ribs are removed from belly pieces by a manual process where an abattoir worker either cuts away the single ribs by a knife or uses a manual rib puller e.g. with a loop-shaped element such as the one described in e.g. CH 597762 or a manual rib puller with a nylon string. Pulling single ribs by a loop-shaped element is also possible with a semiautomatic process e.g. by using a device as described in EP 0469680. Using a handheld tool with two knives cutting along a bone is described in CH 604536.

Pulling single ribs as a semiautomatic process using a pneumatic rib puller such as the one shown in FIG. 1, which is a prior art rib puller with a nylon string at the end of the puller makes it possible at a very high speed to pull single ribs from belly pieces when the end of the rib bones are exposed. This is a tough working situation for the abattoir workers as they have to use a finger to locate the string around the exposed end of the rib bone and with the same hand pressing and holding down the rib bone securing the rib bone is not lifted from the meat and does not break. It takes long time to learn to manage a pneumatic rib puller and not everyone can learn to use such a rib puller such as the one shown in FIG. 1, and manage it at the high speed necessary to handle all the belly pieces at the slaughter line. Also, if the string is not in the right position when the pneumatic tool is activated there is a risk of cracking the bone and increasing the number of bone splinters in the meat. The success of the pulling process with the prior art rib puller is depending on the abattoir workers coordination of correct location of the string beneath the exposed end of the rib bone, use of the counter hold to hold the belly piece in a suitable position, activation of the pull bar and support of the rib bone with the hand (carpus) during the pulling of the string, and all this should be done with a high speed.

The hand-held rib puller as described herein is much easier to manage than the prior art rib puller and it also reduces the working stress imposed upon the abattoir workers as it is much easier to bring the string in the correct position and also the pressure applied by the abattoir workers towards the belly meat pieces is very much reduced thus reducing the risk of physical disabilities for the abattoir workers.

For some kinds of meat cuttings machines have been developed which in a pure mechanically pattern remove bones from cuttings. Such machines are often removing a pre-determined amount of a cutting which may not be adjusted due to the variation in the meat cuttings such as variation in size of the bones and of the meat cuttings themselves. Too much meat may be removed in such a bone removal, which may add up to a huge amount of products which are sold at a lower price due to a lower weight.

In the automation of the process of removing bones from carcasses and cuttings, measuring systems are required to obtain information which can be used e.g. when the bone removing part of a system such as a robot removes the bones.

Herein is described a measuring or scanning system for determining presence and/or position of bones in a meat piece and especially of bones located near the edge in a meat piece, such as ribs in a belly piece. The measuring system may be a part of a larger system for removing detected bones, where the bones are automatically removed by an industrial robot. Such a system may be a system for removing near the edge bones e.g. ribs from a belly piece.

The rib puller as described herein may be constructed as a pneumatic rib puller and also as a tool for a robot such as an industrial robot. A measuring system for determination of the presence and location of bones such as ribs is also described, this measuring system can collect information and determine a working path which an industrial robot uses when removing bones from a meat piece such as ribs from a belly piece.

SUMMARY OF INVENTION

Disclosed is a device for loosening bones from a meat piece such as for loosening ribs from a belly piece of a slaughtered animal where at least one end of the bones such as ribs are exposed, the device comprises
- at least one counter hold for supporting the device towards the meat piece such as towards the belly piece at an area which is with or close to non-exposed ends of the bones such as ribs, and
- at least one longitudinal movable pull bar, and
- at least one string for loosening a bone such as a rib when being pulled along the bone, where the string is fastened to the pull bar for pulling the string in a direction towards the counter hold, and
- optionally at least one longitudinal holding-down bar for holding down at least one bone such as a rib while loosening this bone, where the holding-down bar is substantially parallel to the pull bar and has a length corresponding at least to the length of the pull bar.

When in function the string is pulled along and beneath a bone hereby loosening the bone from the meat.

The device may further comprise at least one loading means located close to said string when the device is not in function, where the loading means is for securing feeding of the string around an exposed bone before loosening the bone.

The device may also comprise at least one loading means located at the end of the holding-down bar such that the string at least partly can surround the loading means when not in use and where the loading means is for securing feeding of the string around an exposed bone such as a rib before loosening the bone.

The loading means may have a cavity suitable to be positioned around an end of an exposed bone such as a rib end before loosening the bone, and the loading means may have a sharp edge along an entrance to the cavity.

The counter hold of the device may be a non-movable support such as a plate to be located towards a meat piece and/or the counter hold may comprise at least one movable support such as at least one vertically movable rod or element. The counter hold may also be at least one plate with pointed tips such as pins or spikes, herein just denoted pins.

The device may be a hand-held device and may by connected to a motor for activating the pull bar, where the motor may be an electric motor or a pneumatic system, or the device may be connected to and managed by a robot, such as an industrial robot.

Also disclosed is a bone loosening or bone removing system which may comprise:
  The device or tool as described herein, wherein the device further comprises robot connecting means such that the device constitute a robot tool, and
  A robot such as an industrial robot with at least one working arm suitable for connecting the robot tool to the working arm and suitable for managing the robot tool in a process for loosening bones from a meat piece such as loosening ribs from a belly piece of a slaughtered animal, and
  At least one scanner or measuring system for obtaining scanning information when scanning at least one meat piece to localize the presence and/or location and/or size of any bones such as ribs being located close to the surface of each of the at least one meat piece, wherein said scanner may be a measuring system with at least one light source and at least one camera and where light is directed towards a meat piece and the light reflected and/or directed through the meat is detected and
  At least one processor for processing the scanning information in respect of each of the scanned meat pieces and for computing working paths for the robot working arm including the robot tool, and
  A robot arm controller for managing the at least one robot working arm based on working paths information received from the processor, and
  Optionally a conveyor belt for conveying the at least one meat piece.

When in use the device or system may be managed in a method for loosening at least one bone from a meat piece such as for loosening at least one rib from a belly piece of a slaughtered animal where at least one end of the bones such as ribs are exposed, the method comprising placing the device with the holding-down bar above and substantially parallel with a bone such as a rib which is to be loosened or removed and with the string in front of the exposed bone end such as a rib end and activating the pull bar whereby the string is pulled by the pull bar towards the counter hold and hereby loosening or releasing the at least one bone such as at least one rib at least along part of the longitudinal direction of the bone.

The invention also relates to a measuring system or a scanning system with sources for emitting electromagnetic waves such as light and receiving sensors such as cameras. Light of different wavelengths such as blue/green light and red/infrared light can be directed towards a meat piece and the reflected blue/green light and the emitted red/infrared light can be registered such as by line scanning. From constructed images the presence, position, lengths and angles of bones located near an edge of a meat piece can be determined. Such information can be communicated to e.g. an industrial robot with a robot tool for loosening bones and the robot may loosen or remove the identified bones.

The measuring process performed by the measuring system may be performed while the meat piece is conveyed by a conveyor belt and the measuring system preferably is non-moving. Removal of bones by an industrial robot may be performed on a stationary meat piece or on a meat piece being conveyed e.g. on a conveyor belt.

Described is also a measuring system for determining the presence and/or positon of at least one bone in at least one meat piece while the meat piece or the measuring system pass the location of each other such as when a meat piece is conveyed on a transport surface such as on a conveyer belt, and where the measuring system optionally further is for determining the length and/or orientation of the at least one bone, the system comprises
  At least one first source for emitting electromagnetic waves where the electromagnetic waves are emitted from above and towards the meat piece when the measuring system is in function and such that the emitted electromagnetic waves is directed towards at least a first side of a meat piece,
  At least one second source for emitting electromagnetic waves where the electromagnetic waves are directed towards at least a second side of the meat piece when the measuring system is in function,
  At least one receiving sensor such as a camera facing towards the meat piece when the measuring system is in function and where the at least one receiving sensor receives and separates electromagnetic waves in at least two groups of wave ranges, and where the at least one receiving sensor receives electromagnetic waves being directed in a direction upward according to the meat piece, and the received and recorded electromagnetic waves are obtained from at least part of the meat piece,
  At least one processing unit such as a PLC for processing at least some of the electromagnetic waves received by the at least one receiving sensor and where at least two images or datasets are constructed from the at least two groups of wave length ranges and based on the at least two images or datasets the presence and/or position and optionally length and/or orientation of the at least one bone is determined.

The light used in the measuring system may be light waves in the blue or green region such as light with wave lengths of between about 430-500 nm or 500-565 nm and light waves in the red region including infrared region such as light with wave lengths of between about 620-1000 nm.

A guide may guide a red light source along a side of a meat piece which is orthogonal to the upper surface of the meat piece during the measuring process and such that the red light waves are directed towards the meat piece in a predetermined distance from the upper surface of the meat piece. The guide can secure that this distance is constant along the entire meat piece. The meat piece should be oriented with the upper surface upward i.e. such that the bones to be loosened or removed and which preferably is near an edge in the meat piece upper surface is facing upward.

Described is also a method for determining the presence and/or positon of at least one bone in at least one meat piece while the meat piece is conveyed such as on a conveyer belt and where the method optionally further is for determining the length and/or orientation of the at least one bone, the method comprises
  Conveying at least one meat piece on a transport surface of a conveyor belt, Directing electromagnetic waves such as blue and/or green wave lengths towards a first surface of the at least one meat piece, Directing electromagnetic waves such as red and/or infrared wave lengths towards a second surface of the at least one meat piece, Receiving electromagnetic waves of at least one predetermined wave range such as blue and/or green wave lengths and which are reflected from the first surface Receiving electromagnetic waves of at least one predetermined wave range such as red and/or infrared wave lengths and which are transmitted through the meat piece and emitted from the first surface of the meat piece, Processing the received electromagnetic waves to construct at least two images or datasets which may be superposed over each other such that one image or dataset is constructed and which indicate the presence and/or position of at least one bone in the meat piece.

Described is also how the measuring system may be combined with a system including an industrial robot and where this robot can loosen or remove bones such as ribs from a belly piece based on information communicated from the measuring system.

DETAILED DESCRIPTION OF THE INVENTION

Figure 1:
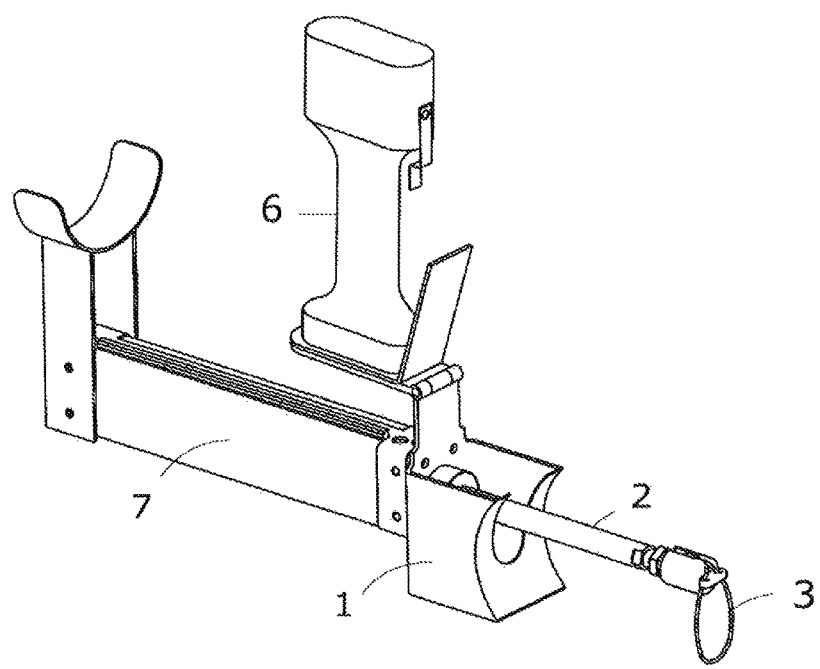
FIG. 1 illustrates a prior art pneumatic rib puller.

An aspect of the invention relates to a device for loosening bones from a meat piece such as for loosening ribs from a belly piece of a slaughtered animal where at least one end of the bones, such as the end of ribs are exposed, the device comprises At least one counter hold for supporting the device towards the meat piece such as a belly piece, and At least one longitudinal movable pull bar, and At least one string suitable for loosening a bone such as a rib when the string is being pulled along the bone, where the string is fastened to the pull bar for pulling the string, and At least one longitudinal holding-down bar for holding down at least one bone such as a rib while loosening this bone, where the holding-down bar is substantially parallel to the pull bar and/or At least one loading means located close to the string when the device is not in function, and Optionally a first handle to hold the device.

The counter hold may support the device towards the meat piece at an area of the meat piece which is opposite the exposed ends of the bones such as at the area which is with or close to non-exposed ends of the bones e.g. ribs, or close to e.g. the spinal column or in at least one area beside a bone to be loosened or removed. The at least one counter hold may also support the device towards the meat piece in an area besides a bone to be loosened or removed.

The pull bar may pull the string in a direction towards the counter hold or in a direction passing the at least one counter hold.

The holding-down bar may have a length corresponding at least to the length of the pull bar.

The device as described herein is preferably a rib puller but may also be suitable to loosening or remove other types of bones from slaughtered animals. Preferably a slaughtered animal is cut into smaller pieces before loosening and optionally removing at least one bone with the device as described herein. Most preferably the rib puller is used to loosen or remove at least one rib from a belly piece where the rib ends are being exposed when a cut is performed substantially parallel to the spinal column hereby the ribs with cut ends have an angle to the cutting line of between 10-60°, such as between 15-50°, e.g. between 20-40°, such as between 20-30°, e.g. about 25°.

Preferably meat pieces such as belly pieces are located with the surface to be analysed facing upward in the processes of scanning the meat pieces and/or loosening the bones with a device as described herein.

The slaughtered animal may be a wild animal or a domesticated animal. Preferably the slaughtered animal is selected from the group of pigs, cattle, dairy cows, game, sheep, deer, lamb. Most preferably the slaughtered animal is a pig.

The term belly piece should be understood to comprise any size of a meat piece originating from the belly part of a slaughtered animal and comprising at least one rib. In most situations such as at slaughterhouses a belly piece comprises at least two ribs such as at least five ribs, such as at least ten ribs, such as all the ribs of half a carcass.

As an example a pig belly piece may include all the ribs of one side of the pig and the belly piece can be e.g. 60-70 cm long and 20-30 cm wide, though the dimensions are dependent on the size of the pig, and where the width is determined by a cut along the spinal column and a second cut through the ribs, and which cuts are substantially parallel to the spinal column. The number of ribs which should be loosened or removed from a pig belly piece may be at least one, e.g. 1-15, such as 2-9, e.g. 10-12 such as 11, and which may be of a length between about 1.5 cm and about 20 cm when the pig belly piece is cut as described just above.

The counter hold may comprise a non-movable support or a movable support which can be movable in a direction (e.g. along the Y-axis) substantially perpendicular to the working direction of the pull bar (e.g. along the X-axis) and such that the meat piece may have its spinal column in the third direction (e.g. along the Z-axis). When the device is used for loosening ribs the counter hold can be located close to the spinal column of the belly piece to hold and support the meat piece securing the meat piece does not move substantially while at least one rib is loosened by the at least one string of the device. The counter hold may thus be a plate and/or comprises at least one vertically movable rod or element. The counter hold may also be at least one plate with pins which is positioned on the top part of the meat piece when a bone should be loosened from the meat piece.

A movable support of the counter hold may comprise different elements being individually movable e.g. as indicated in the figures with movable rods, hereby the counter hold may adjust to the shape of the meat piece which should be supported and thus increase the strength of the support. The individually movable elements of a movable support also make it easier for a user such as an abattoir worker or a robot such as an industrial robot to use the device as it is not requested that the entire counter hold is positioned in a specific position in respect of the spinal column, as the elements adjust to the shape of the meat piece.

The pull bar may comprise a string mounting device to attach a string to the pull bar. Such mounting devices are known in the art.

Figure 5:
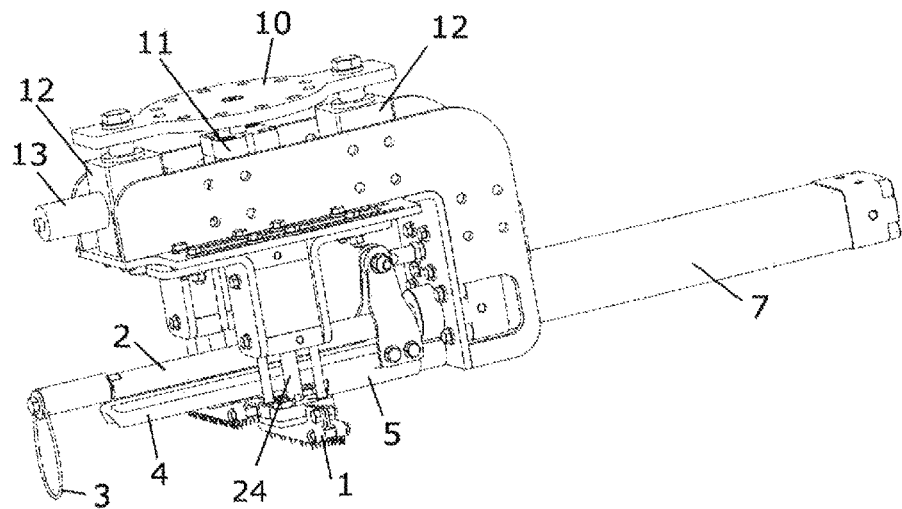
FIGS. 5 and 6 illustrates a rib puller for an industrial robot, where the rib puller is in the end position.

The holding-down bar which is for holding down at least one bone such as at least one rib while loosening this bone should be strong enough to hold down any bone which lift itself upward as the string is pulled along this bone and loosening it from the meat. It may be important to hold down the bones to be removed to avoid the bone lift itself from the meat or to avoid the bone breaks. Especially ribs which are porous in structure may easily break, which should preferably not happen as this may interrupt or prolong the process of loosening the ribs in a belly piece. Preferably the holding-down bar is a little longer than the pull bar when the device such as a hand-held device is in a position ready to have the string being directed beneath an exposed bone end, whereas for a robot tool the holding-down bar may be shorter than the pull bar as illustrated in FIG. 5, as in this position the string is under a bone such as a rib and this bone will secure the string stays under the holding-down bar when the pull bar is returned to its start position. The holding-down bar may have any suitable form when observed in a transverse cut of the bar, such as circular, oval, U-shaped e.g. inverted U-shaped, squared or rectangular. The holding-down bar may also be a loading means such as a loading means of a robot tool. The loading means may be capable of holding down a bone to be loosened during the process of pulling a string along the bone.

The device may further comprise at least one loading means each located at the end of the holding-down bar and such that the string connected to the pull bar at least partly can surround the loading means when the device is not in use and where the loading means is for securing feeding of the string around an exposed bone such as an exposed rib before loosening this bone. For a robot tool the loading means may also be located at the end of the holding-down bar where this 'end' may be the end connecting the holding-down bar to the remaining part of the robot tool.

The loading means may have a cavity suitable to be positioned around an exposed bone before loosening the bone, hereby the loading means may be fully or partly hollow securing an exposed bone end can enter into the cavity, and at the same time secure the strength of the loading means. The loading means may have a sharp edge along an entrance to the cavity such that when the loading means is loaded on an exposed bone end the sharp edge of the loading means cut into the meat and/or membranes beneath the bone such as a rib securing a proper loading onto the bone end and thus securing the proper location of the string when being pulled by the pull bar and thus the string will be directed along and beneath the bone hereby loosening the bone. For a robot tool the cavity on the loading means may be present all the time or may only be present from just before the time where the loading means is positioned to encircle a cut end of a bone such as of a rib, this may be performed by activating the holding-down bar which may be moveable in its longitudinal direction and moving/pushing it a little forward to create the cavity. The cavity may be about 0.5-2.5 cm deep, such as 1-2 cm deep, e.g. 1-1.5 cm deep, such as 0.5-1.5 cm. A cavity of a loading means may also be present when a cleaning plug being located inside of the loading means is retracted or the loading means is moved slightly forward in front of a cleaning plug prior to positioning the loading means in front of an exposed bone end.

Especially the hand-held device may further comprise a second handle which can be connected to the holding-down bar and/or to the loading means in the area where the string is located when the device is not in use or the second handle is located in the area of the loading means and this area of the device can be denoted the loading end. The second handle is thus located at the end of the device which will be above the exposed bone ends when in use. With such a second handle on the device the abattoir worker controls the device with both hands, one hand on a grab (the first handle) for carrying the device and activating a trigger when the pull bar should be activated and the other hand on the second handle for controlling the loading of the loading means onto at least on exposed bone end.

A second handle may be demountable connected to the holding-down bar and/or to the loading means such that the second handle can be demounted when the string should be replaced with a new string and the second handle can be mounted again after the string is replaced. The second handle may also have a size and form allowing replacement of the string on the pull bar without demounting the second handle, this is preferred as the string may be used up within a few hours and a new string should be mounted more times each day.

The device as described herein may be connected to a motor capable of being activated for pulling or pushing the pull bar from a start position to an end position and hereby pulling the string along a bone such as a rib. The motor may be an electric motor or a pneumatic system. The device when connected to a motor or a pneumatic system may be a hand-held system to be operated by an abattoir worker or the device may be connected to a robot, such as an industrial robot and be operated as a robot.

The device is preferably made of a strong material acknowledged to be used for handling food. Preferably at least the counter hold, the pull bar, the holding-down bar, and the loading means are made of a metal, such as steel such as stainless steel. The string is preferable made of a strong and flexible material e.g. nylon.

The device may comprise at least two substantially parallel sets of pull bars each including a string and holding-down bars, such as two or three sets, and each set comprises features as described herein. These sets may each further include a loading means. Hereby at least two, such as e.g. two or three bones or ribs may be loosened at a time i.e. simultaneously, partly simultaneously or in sequence where the second loosening process is initiated e.g. at a pre-determined period after initiation of the first loosening process. Such a device with multiple sets of pull bars and holding-down bars may be hand-held or connected to a robot as described elsewhere herein for the robot tool. The sets with pull bars may be individually adjustable laterally such that the distance between the loading means and/or holding-down bars may be adjusted and correspond to the distance between ribs to be loosened or the cut rib ends of these ribs and/or be adjusted to the angle of each of these ribs. One pull bar and one holding-down bar may be used with two or three loading means and two or three strings, however it is preferred that sets of e.g. two pull bars, two holding-down bars and/or two loading means and two strings are used, which makes individual loosening of ribs possible, where the pull length when pulling or drawing the string along a rib can be determined in respect of the length of each rib. The individual sets also makes it possible to adjust the pull bar, the holding-down bar and/or the loading means to the angling of each rib and/or to an optimal positioning of the loading means in front of a cut rib end, and to the distance between two neighbor sets.

The device as described herein may be a tool such as a rib puller suitable to be mounted on an industrial robot which can manage the rib puller to pull at least one rib from a meat piece such as from a belly piece.

The dimensions of the device such as length of pull bar and/or holding-down bar and/or length and inner diameter of the loading means may be determined in respect of the type of bones such as ribs which should be loosened, as well as in respect to the animal race and age i.e. size of the animal, and thus to the size of the bones in the carcass.

An aspect of the invention relates to a robot tool in the form of a rib puller for an industrial robot, such a robot tool may comprise
 at least one attachment device for connecting the device to an industrial robot,
 at least one counter hold capable of being pressed towards a meat piece,
 at least one movable pull bar,
 at least one string mounting device at the pull bar or a string for loosening a bone, and
 at least one loading means.

The at least one loading means may also be capable of holding down the bone during the process of pulling the string along the bone to loosen the bone.

The robot tool may also comprise
 at least one counter hold for supporting the device towards the meat piece such as towards the belly piece at an area which is with or close to non-exposed ends of the bones such as ribs or in at least one area beside a bone to be removed, and
 at least one longitudinal movable pull bar, and
 at least one string for loosening a bone such as a rib when being pulled along said bone, where said string is fastened to the pull bar for pulling the string in a direction towards the at least one counter hold and optionally past the at least one counter hold, and
 at least one longitudinal holding-down bar for holding down at least one bone such as a rib while loosening this bone, where said holding-down bar is substantially parallel to said pull bar and has a length corresponding at least to the length of said pull bar and
 a connecting part for connecting the device to an industrial robot.

The features for the robot tool may be very much like the features for the hand-held tool and the description herein in relation to the hand-held tool also applies for the robot tool except for the handles on the hand-held tool. For the tools illustrated in the figures the counter holds are located differently in the hand-held device and the robot tool. In respect of the hand-held tool the pull bar is dragged toward the operator operating the tool, whereas in the robot tool the pull bar may be pushed by driving means e.g. a motor such as a pneumatic system, but still the function of the pull bar is to pull the string along a bone however, the robot tool may also be designed such that the pull bar is pulled. The holding-down bar with the loading means in the robot tool may be movable such that it can be pushed slightly forward i.e. in a direction towards a cut rib end and a cavity can be formed at the front end of the loading means which when in function can be used to load the loading means onto the cut rib end hereby encircling the cut rib end. This step of loading the loading means onto the cut rib end is performed manually with the hand-held tool. Part of the robot tool e.g. the pull bar and the loading means on the holding-down bar may be mirrored such that the pull bar is pulled instead of dragged when in function.

The system pulling or pushing the pull bar may be a servo motor and thus making it possible to control the speed of the string being pulled beneath a bone such as being pulled slower at the beginning than at the end of the pull.

As described the holding-down bar or the loading means of the robot tool may be slightly movable such that it can be pushed forward e.g. in relation to a cleaning plug to form a cavity suitable to encircle the cut end of a rib bone. When the holding-down bar or the loading means is in a start position there need not be a cavity in the loading means, as the holding-down bar or the loading means may be moveable. The moving of the holding-down bar or the loading means forward and backward such that the cavity is eliminated between loosening two ribs, secure substantially no meat leftovers is located in the cavity.

The counter hold for the robot tool may be in the form of a plate with pins. The number of these plates may be any suitable to secure the meat piece is kept in position securing the bones can be loosened by the tool, preferably at least one plate is positioned on each side of the pull bar or the holding-down bar. The number and position of the pins on the plates should be such that the meat piece is kept in a firm grip and is preferably not moving during loosening of a bone/rib. The length of pins is preferably 2-3 mm and the number of pins is preferably at least 25 at each plate, such as between 30 and 70, such as about 50. The level of the tips of the pins may be equal for all the pins such that the pins are fixed, however the pins may also be attached to the plate such that the pins are adaptive and adapt to the belly piece such that pins enter more into meat of the meat piece/belly than into bone. The counter hold when holding the meat in the area on each side of a bone such as a rib to be loosened may further have the function of securing the meat bridges or muscle bridges located between the ribs such that these are not removed from the belly piece when ribs are pulled.

The robot tool may comprise an attachment device for attaching the robot tool to a robot arm of an industrial robot. The attachment device may be located anywhere on the robot tool making it possible for the robot tool to function, such as in the upper part of the robot tool, at a side of the tool or at an end of the tool. Side and end is determined in relation to the position and direction of the holding down bar or pull bar.

The robot tool may further comprise a piston to move the tool away from the attachment device, piston guides and a locking plate for shaft securing the tool may stay in the position where the tool is pushed away from the attachment device. Pushing the tool towards the belly piece such as about 1-2 cm secure the holding-down bar is close to a rib to be loosened. The counter hold may be activated by at least one piston pressing the counter hold towards the belly piece.

Figure 4:
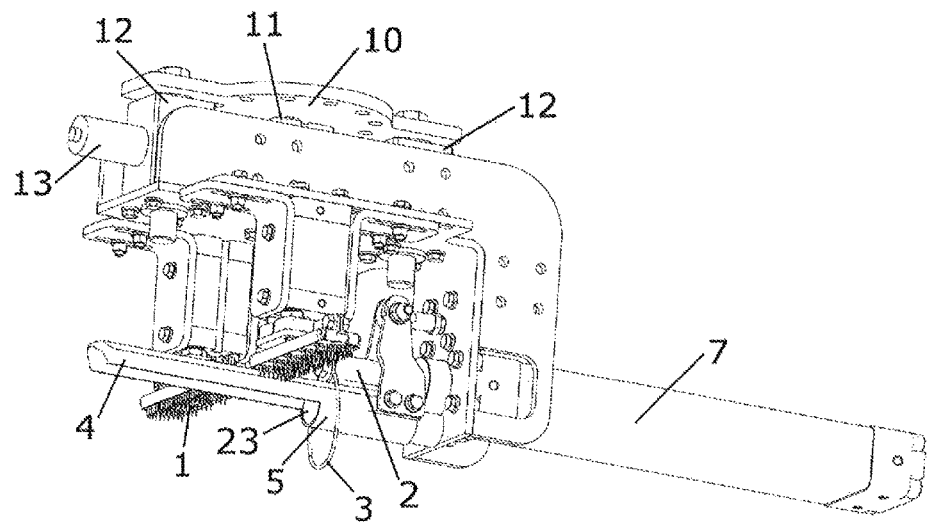
FIG. 4 illustrates a rib puller for an industrial robot, where the rib puller is in the start position.
Figure 6:
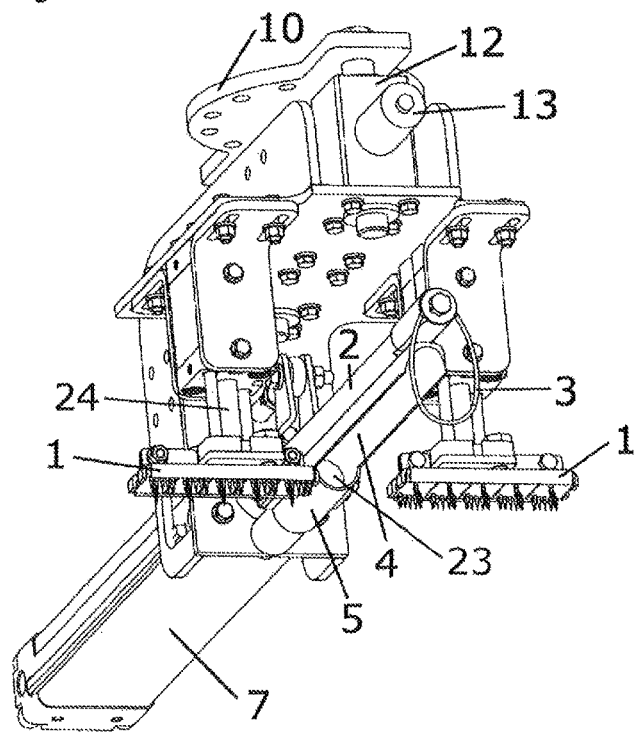

The robot tool as illustrated in FIG. 4-6 is working from the side of a belly piece where the rib ends are cut such that the pull bar is pushed forward to pull the string along a bone. The robot handles the robot tool based on information received from a measuring or scanning system such as a measuring or scanning system described below.

An aspect of the invention may relate to an automatic system for loosening at least one bone from a meat piece such as at least one rib from a belly piece of a slaughtered animal, such an automatic bone loosening and/or bone removing system may comprise

- A robot tool comprising a device as described herein for loosening bones from a meat piece such as ribs from a belly piece of a slaughtered animal where the device further comprises robot connecting means such that the device constitute a robot tool,
- A robot, such as an industrial robot with at least one working arm suitable for connecting the robot tool to the robot arm and suitable for managing the robot tool in a process for loosening bones from a meat piece such as ribs from a belly piece of a slaughtered animal,
- At least one scanner or measuring system for obtaining scanning information when scanning at least one meat piece to localize the presence and/or location and/or size of any bones such as ribs being located close to the surface of each of the at least one meat piece,
- At least one processor for processing the scanning information in respect of each of the scanned meat pieces and for computing working paths for the robot arm including the robot tool,
- A robot arm controller for managing the robot arm and robot tool based on working paths information received from the processor,
- Optionally a conveyor belt for conveying at least one meat piece.

The robot arm controller may be included in the at least one processor.

The robot may be an industrial robot which is automatically controlled, reprogrammable, and has a multipurpose manipulator programmable in three or more axes.

When in function the robot may perform all the work of loosening ribs from a belly piece i.e. loosening all the ribs, or one or two ribs may be removed manually before the robot removes or loosen the remaining numbers or a predetermined number of the ribs from the belly piece. An abattoir worker may remove one or two ribs manually and simultaneously loosen and remove the pleura covering the belly piece above the ribs, and afterwards the robot loosen or remove the remaining numbers or a predetermined number of ribs e.g. by loosening 1, 2 or 3 ribs at a time. An abattoir worker may also remove only odd bones and the pleura before the robot loosen the remaining ribs of a belly piece.

The robot may be capable of loosening or removing at least one rib such as in total 3-14 ribs from each belly piece from at least 300-550 belly pieces per hour.

Another aspect of the invention relates to a method for loosening at least one bone from a meat piece such as at least one rib from a belly piece of a slaughtered animal where at least one end of the bones are exposed, the method comprising placing a device as described herein with at least one holding-down bar or pull bar above and substantially parallel with at least one bone which is to be loosened or removed and with the at least one string in front of the exposed bone end(s), activating the pull bar(s) whereby the string(s) is/are pulled by the pull bar(s) e.g. towards the counter hold and hereby loosening or releasing the at least one bone at least along part of the longitudinal direction of the bone.

The method may comprise loosening or removing one or more ribs at a time, such as two, three or four ribs at a time. The method may be performed with a hand-held device or with a device mounted on a robot. Preferably a robot can loosen one, two or three ribs at a time. With a robot system with a device capable of loosening at least two bones at a time, the distance between the loading means may be adjusted in respect to information obtained from a scanning as described elsewhere herein. Such a distance adjustment may be performed automatically.

The method may comprise the steps of 1. Scanning the meat piece to obtain information regarding the presence, location and/or size of at least one bone, 2. Loosening or removing at least one bone with the device as described herein and wherein the loosening/removing process uses scanning information obtained in step 1.

If the meat piece to be handled in the method comprises a membrane above the at least one bone to be loosened or removed, the method may comprise the steps of 1. Loosening or removing a membrane which at least partly covers at least one bone to be removed, 2. Loosening or removing at least one bone with the device as described herein. This method is preferably performed with a hand-held device.

The method may further comprise a scanning step, such that the method may comprise the steps of 1. Loosening or removing a membrane which at least partly covers at least one bone to be removed, 2. Scanning the meat piece to obtain scanning information as further described herein, 3. Loosening or removing at least one bone with the device as described herein.

A membrane which at least partly covers at least one bone to be removed may be loosened or removed manually or automatically. The membrane may be pleura when the meat piece is a belly piece.

For removing/loosening at least one bone from belly pieces where the ribs are cut through by a saw which makes exposed ends of the ribs, the method may comprise the steps of:

1. Orientating at least one belly piece on a conveyor belt with the skin towards the belt and with the cut side with exposed rib ends of all belly pieces along one predetermined side of the conveyor belt when considered in the direction of motion,
2. Removing or loosening at least part of the pleura,
3. Conveying the at least one belly piece along a measuring or scanning system scanning one belly piece at a time and obtaining scanning information as described elsewhere herein,
4. Conveying the at least one belly piece to a handling station where at least one rib is loosened or removed automatically by a robot, and the loosening or removing of at least one rib is based on scanning information obtained in step 3,
5. Conveying the belly piece away from the handling station,
6. Optionally removing loosened ribs and/or ribs not loosened in step 4, wherein step 1 and 2 can be performed in any order.

The belly pieces may in the method just describe originate from right or left side of animals such as from pigs and may be placed with these right and left side belly pieces in any order on the conveyor belt.

In an aspect the invention also relates to use of the device described herein for loosening or removing at least one bone from a meat piece such as at least one rib from a belly piece of a slaughtered animal where at least one end of the bones are exposed. The use may be with a hand-held device or with a device mounted on a robot, such as an industrial robot.

When loosening bones such as ribs with the robot tool the string may be pulled along the bone to a certain point, which may be determined by a measuring system. Such a certain point may for ribs be until the feather bone or substantially until the feather bone. As the ribs of a belly piece are not of equal length the location of the feather bone may be determine for each rib to be loosened or removed.

A rib puller for an industrial robot is illustrated in FIG. 4-6. Before this rib puller is activated to remove ribs from a belly piece, the membrane (pleura) located above the ribs is preferably at least partly removed and the belly piece is analyzed such as be a measuring or scanning system as described below to determine the presence and/or position such as length and/or orientation of ribs in the belly piece.

The rib puller for an industrial robot can when in function be described by performing the following steps after it has received the working paths from the measuring system described below, and the working path is preferably received at least for the first rib to be loosened and subsequent or simultaneous for the following ribs to be loosened:

1. The rib puller is in a waiting position where the pull bar with the string is drawn back with the pull bar within the motor such as a pneumatic system, the counter hold is located in a position above the holding-down bar or the movement path of the pull bar, and the attachment device for connecting the tool to an industrial robot is in a withdrawn position. The tool in a waiting position or start position is shown in FIG. 4.
2. Optionally, when the rib puller is located above a rib in a belly piece the contact with the belly piece is establish by activating the pistons located close to the attachment device such that the entire tool is pushed towards the belly piece.
3. The belly piece is maintained in position by activation the pistons pushing down the counter hold such that the pins make a firm connection with the belly piece.
4. The loading means is loaded onto an end of a rib: The holding-down bar with the loading means is moveable such that when the holding-down bar is in position ready to be loaded on a cut bone end, the holding-down bar with the loading means is moved forward and the loading means encircles the cut end of a rib bone herby securing the string will be pulled along the rib to be loosened.
5. The motor activates the pull bar and the string is pulled along the rib until it reaches the feather bone or just before it reaches the feather bone and hereby loosening the rib. The tool in an end position is shown in FIGS. 5 and 6.
6. The tool returns to the start position by doing the steps in reverse order: deactivating the pull bar i.e. returning the string, returning the loading means, de-activating the pistons controlling the counter hold, and optionally deactivating the pistons located close to the attachment device and hereby lifting the entire tool such as a few centimeters above the belly piece.
7. Moving the tool to another rib to be loosened and place the holding-down bar at an angle similar to the rib to be loosened and then repeating the steps 2-6.
8. The process steps can be repeated until all the ribs in a belly piece are loosened or until a pre-determined number of ribs in a belly piece are loosened.

The robot tool may be constructed and/or handled such that step 2 can be omitted.

The process with the robot tool may be performed on non-moving meat pieces or meat pieces being conveyed by a conveyor belt. The speed of a conveyor belt may be e.g. between 50-100 mm/sec, such as about 50 mm/sec.

A measuring or scanning system may also be part of an automatic system for determining the presence and/or positon of at least one bone in at least one meat piece while the meat piece or the measuring system pass the location of each other such as when a meat piece is conveyed on a transport surface such as on a conveyer belt, and where the measuring system optionally further is for determining the length and/or orientation of the at least one bone, the system may comprise a. At least one first source for emitting electromagnetic waves where the electromagnetic waves are emitted from above and towards the meat piece when the measuring system is in function and such that the emitted electromagnetic waves is directed towards at least a first side of a meat piece,
b. At least one second source for emitting electromagnetic waves where the electromagnetic waves are directed towards at least a second side of the meat piece when the measuring system is in function, and this second side is preferably not from below,
c. At least one receiving sensor such as a camera facing towards the meat piece when the measuring system is in function and where the at least one receiving sensor receives and separates electromagnetic waves in at least two groups of wave ranges, and where the at least one receiving sensor receives electromagnetic waves being directed in a direction upward according to the meat piece, and the received electromagnetic waves are obtained from at least part of the meat piece,
d. At least one processing unit such as a PLC for processing at least some of the electromagnetic waves received by the at least one receiving sensor and where at least two images or datasets are constructed from the at least two groups of wave length ranges and based on the at least two images or datasets the presence and/or position and optionally length and/or orientation of the at least one bone is determined.

The measuring system may be located on or connected to a conveyor belt to scan meat pieces such as belly pieces located on the conveyor belt. After scanning of a meat piece, it may be conveyed by a conveyor belt to a location where an industrial robot may loosen the bones.

It is believed that the measuring system will be most used for examination of meat pieces being conveyed on a transport surface such as on a conveyor belt and such that the measuring system when ready to use is a stationary measuring system mounted on a conveyor belt. The invention will be described as a stationary measuring system on a conveyor belt, but may as described above be a moving measuring system where the meat pieces is not moving during the examination, thus the description should be understood for both situations.

With a stationary measuring system this system can be described to be a measuring system for determining the presence and/or positon of at least one bone in at least one meat piece while the meat piece is conveyed on a transport surface such as on a conveyer belt and where the system optionally further is for determining the length and/or orientation of the at least one bone, the system may comprise at least one first source for emitting electromagnetic waves where the electromagnetic waves are emitted from above and towards the transport surface and such that the emitted electromagnetic waves are directed towards at least a first side of the meat piece when the meat piece is being transported past the first source for emitting electromagnetic waves,
at least one second source for emitting electromagnetic waves where the electromagnetic waves are directed transversely across and close to the transport surface in a height above the transport surface such that the emitted electromagnetic waves are directed towards at least a second side of the meat piece when this meat piece is being transported past the second source for emitting electromagnetic waves, preferably this second side is not the side being in contact with the conveyor belt, at least one receiving sensor such as a camera facing from above and towards the transport surface and which can receive and separate electromagnetic waves in at least two groups of wave ranges, and where the at least one receiving sensor receives electromagnetic waves being directed in a direction upward according to the transport surface, and the received or recorded electromagnetic waves are obtained from at least part of a meat piece being transported on the transport surface, at least one processing unit such as a PLC for processing at least some of the electromagnetic waves received by the at least one receiving sensor and where at least two images or datasets are constructed from the at least two groups of received wave length ranges and based on the at least two images or datasets the presence and/or position and optionally length and/or orientation of the at least one bone is determined.

For the at least one receiving sensor it is to be understood that when receiving electromagnetic waves this also means that the electromagnetic waves are recorded by the system making it possible for a processing unit to analyse the recorded data sets.

The measuring system may comprise a conveyor belt for conveying at least one meat piece where the conveyor belt has a transport surface where the at least one meat piece is located while determining the presence and/or position of bones in the meat piece. The system may also be a system without a conveyor belt and/or may be integrated in a measuring bow as described below which can be connected to a conveyor belt.

The measuring system is based on using electromagnetic waves such as light of at least two different wavelengths where the one type of electromagnetic waves is directed from a source towards the surface of a meat piece preferably towards the upper surface and the reflected electromagnetic waves are recorded. The other type of electromagnetic waves is directed towards and into the meat piece from one side of the meat piece which is preferably not from below and the electromagnetic waves of similar type emitted from another side such as perpendicular to the side for entrance of the electromagnetic waves of the meat piece is recorded. The two types of data sets or images registered by one or more sensors such as cameras are processed to determine presence and/or positon of at least one bone in at least one meat piece.

Meat pieces which can be examined and further handled by the robot system described herein may be meat pieces from any animal such as from pig, cow, cattle, deer, game, sheep, goats, poultry such as chicken. Any type of meat pieces may be examined by the system, preferred is meat pieces with bones near the surfaces of the meat piece, such as meat pieces with ribs, loin with ribs, neck fillet with bones, ham with bones, fore-end or shoulder with shoulder blade. The system is especially suitable for analyzing and handling belly pieces with ribs from pork, cow/cattle, sheep, goat, deer, game etc. Bones near the surface of a meat piece is preferably located at least with a bone part within 2 cm from the meat surface, such as within 1.5 cm, e.g. within 1 cm, e.g. 0.5 cm. The bones to be loosened or removed are preferably less than 5 cm in diameter, such as less than 4 cm, e.g. less than 3 cm, such as less than 2 cm, such as less than 1.5 cm. The location in the form of depth within the meat of the bones suitable to be detected by the system and method as described herein may depend on the type of meat such as color and whether only meat is located between the bone and the meat surface or whether fat, membranes and/or tendons are also located between the bone and the meat surface. The meat between the bone and the meat surface should preferably be penetrable to at least some of the electromagnetic waves e.g. red light directed into the meat.

The at least one receiving sensor may be a first receiving sensor such as a camera recording light in the blue and/or green wavelength region and is denoted a 'blue camera'. A second receiving sensor may be a camera recording light in the red and/or infrared wavelength region and is denoted a 'red camera'. The at least one receiving sensor may be one camera capable of receiving and separating light in the blue and/or green wavelength region as well as in the red and/or infrared wavelength region. By separating is meant that data such as line scan data from some of the blue and/or green lines and from some of the red and/or infrared lines are forwarded to a programmable controller in an amount suitable to perform the analysis of the images or data sets and determine the presence and/or positon of at least one bone in a meat piece. Preferably the receiving sensor(s) perform line scanning with e.g. about 100 lines per second. Afterwards the lines are connected into images from where the presence and/or positon of at least one bone is determined.

The measuring system may further comprise a first meat piece sensor for determining the presence of a meat piece being transported past a first position on the transport surface of the conveyor belt. The function of the first meat piece sensor is to initiate the sources for emitting electromagnetic waves such as lights and to initiate the receiving sensor(s) such as camera(s) to record electromagnetic waves such as lights. The first meat piece sensor may also record the length of a meat piece passing by the sensor e.g. by using the time the meat product uses to pass by the first meat piece sensor together with the speed of the conveyor belt.

The at least one first source for emitting electromagnetic waves may emit light waves in the blue or green region such as light with wave lengths of between about 430-500 nm or 500-565 nm. This first source for emitting electromagnetic waves is denoted 'blue light source'. Light with blue wavelengths of about 430-500 nm is preferred rather than green light, as blue light gives a better contrast in the images than the green light when determining position of bones.

The blue light source is preferably positioned above a conveyor belt for transporting meat pieces to be examined. The blue light source preferably produces a blue line across the entire meat piece and perpendicular to the transport direction. The blue light source may be any light source emitting light in the blue or green regions or wavelengths, preferably LED or laser. If using a light source with multiple wavelengths a filter may be use in the blue camera. If using a blue laser no filter is need in the blue camera and the effect is higher than if a filter is used. The light should be capable of being directed into a line.

The camera recording blue light is preferably a camera suitable to perform line scanning. Preferably the camera recording blue light can perform line scanning by recording lines based on light with wavelengths only in the blue and/or green region or the camera may record light of all wavelengths being present and a filter in the camera removes all other wavelengths except the pre-determined ones in the blue and/or green region. A predetermined narrow band of wavelengths may be recorded by the blue camera. The camera recording blue light will be able to record the length and angle of bones located close to the surface of a meat piece as bones and fat are light and thus reflects the blue light. The camera recording blue light may be positioned just above (~0 degree) the meat piece to be examined or within 40 degree counter clock wise, which is further explained below in respect of the camera recording red light. The camera recording blue light should preferably be able to receive reflected blue light along the entire length of the bones to be examined, which may or may not correspond to the width of the meat piece being examined.

The at least one second source for emitting electromagnetic waves may emit light waves in the red region including infrared (IR) region such as light with wave lengths of between about 620-1000 nm. This second source for emitting electromagnetic waves is denoted 'red light source'. The red light source is used for detecting the end of the bones such as the cut ends of bones in belly pieces where the ribs are cut across. The red light waves are preferably directed into the meat from one side of the meat piece where the red light will disperse within the meat, which for many animals also is red, and the light will be visible in meat parts only when observed from another side of the meat piece such as a side which is perpendicular to the side where the red right were directed into the meat. Preferably red light is not directed towards the meat piece from below. Light in the red wave region may be directed towards the meat along the entire side of the meat piece, however at a certain moment in time preferably only a small part of the meat piece is illuminated with light of red wave lengths. A camera recording red light will be able to produce images indicating areas with red light and these areas corresponds to meat parts of the meat piece whereas areas without red light corresponds to bone parts of the meat piece. Hereby, by registering the meat parts also the bone parts of a meat piece are registered and the presence and end position of bones are then known.

The camera recording red light is preferably a camera suitable to perform line scanning. Preferably the camera recording red light can perform line scanning by recording lines based on light with wavelengths only in the red and/or infrared region or the camera may record light of all wavelengths being present and a filter in the camera removes all other wavelengths except the pre-determined ones in the red and/or infrared region. A predetermined narrow band of wavelengths may be recorded by the red camera.

The cameras recording blue/green and red/IR light may be a single camera capable of recording light of at least blue/green and red/IR light wavelengths.

The measuring system may further comprise a guide for guiding the second source for emitting electromagnetic waves such as a red light past the meat piece such that electromagnetic waves from the second source for emitting electromagnetic waves are directed towards the meat piece in a predetermined distance from the upper side of the meat piece when the meat piece is being transported on the conveyor belt. The red light is preferably a small light with a light emitting area of less than 2 $cm^2$, such as less than 1.5 $cm^2$, e.g. less than 1 $cm^2$, such as less than 0.6 $cm^2$, e.g. less than 0.5 $cm^2$, such as less than 0.4 $cm^2$, e.g. less than 0.3 $cm^2$, such as less than 0.2 $cm^2$, e.g. less than 0.1 $cm^2$. Preferably the light emitted from the red light source will illuminate a spot of about 2-3 cm in diameter and penetrate into the meat. The red light source may be any suitable red light source such as a LED or laser, e.g. a powerful single red LED or laser, and the light source may emit light with wavelengths selected from the red, near infra-red (NIR) or infra-red (IR) regions.

The guide may comprise a holder for the red light source which holds the red light source such that light waves from this light source is directed towards and into the meat piece. The red light source may be with a small lighting area such as a lighting area of less than 2 $cm^2$. The guide may further comprise a kind of ski or slider which can be positioned onto e.g. the upper surface of the meat piece and slide along the meat when the meat piece is conveyed by the transport belt. Preferably the ski or slider possesses a minimal pressure upon the meat piece by only sliding along the meat piece such that the obtained information corresponds to the position of the bones when the slider is no longer on top of the meat piece. The ski or slider may be of any suitable material which may be in contact with meat during a meat processing process. The ski or slider may be about 4-6 cm long, 1-2 cm wide, and 0.5-5 mm thick. The guide may further comprise a spacer located between the slider and the holder for holding the red light source and which may keep a firm distance between the slider and the red light source. The spacer may be adjustable such that the distance between the red light source and the slider can be adjusted such as according to the type and size of meat pieces to be examined. The ski or slider will preferably be located on the top surface of the meat piece being conveyed and will slide along the upper surface of the meat piece and follow the contour of this side, hereby the red light source in the holder can be positioned in a pre-determined distance from the upper surface of the meat piece. The pre-determined distance should preferably be selected such that red light waves emitted from the red light source are directed towards the side of the meat piece e.g. beneath or beneath and onto the location of bone ends e.g. cut bone ends or preferably such that no red light waves are directed in a direction above the upper surface of the meat piece. Securing that substantially all red light waves enter into the meat piece improves the contrast of the obtained images when determining the position of the bone ends close to the side of the meat piece where the red light waves enter into the meat piece. The use of a red light source with a small lighting area results in illumination of only a small part of the meat piece conveyed on the conveyor belt, this gives a better lighting of the meat than if the entire side of the meat is illuminated.

The camera recording red light may be positioned to record light with red wavelengths of similar wavelengths as is used in the red light directed towards the meat, and may be selected from the red, NIR or IR regions of wave lengths. The camera recording red light records light which has passed through the meat and need only register red light in an area of the meat close to the position where the red light source directs red light into the meat piece. Such an area may include the cut ends of bones (this position can be denoted 0 cm) and extend e.g. 5-15 cm along the bones in the meat. For a belly piece with cut ribs the camera recording red light may record light from the first 5-10 cm calculated from the location of the cut rib ends. The camera recording red light may be positioned directly above the area from where it register light or be angled such that the camera is further away from the red light source than if located just above the area from where it register light. If the red light source is positioned at about 90 degree clock wise of a meat piece (the upper part of the meat piece located on a conveyor belt is 0 degree) then the camera recording the red light may be positioned between 0-40 degree counter clock wise (ccw) such as 10-35 degree ccw e.g. 20-30 degree ccw.

The first source for emitting electromagnetic waves such as a blue light source and the first and second receiving sensor such as a blue camera and a red camera may be arranged in a measuring bow suitable to be located above a conveyor belt. The blue and red camera may be only one camera. The cameras are facing downwards and are preferably run in a line scan mode with each line being substantially orthogonal to the transport direction. The second source for emitting electromagnetic waves such as a red light source is preferably located close to the conveyor belt as described elsewhere herein. Meat pieces to be analysed can be conveyed by the conveyor belt and underneath the measuring bow, the distance between the conveyor belt and the measuring bow should be such that electromagnetic waves can be directed towards the meat piece and received from the meat piece. The measuring bow may also comprise the processing unit such as a PLC (programmable logic controller).

The sources for emitting electromagnetic waves and the receiving sensors are all connected by wires or wireless to the processing unit/PLC. The PLC may control the sources for emitting electromagnetic waves and the receiving sensors such as in respect of wavelengths to be emitted and recorded. The PLC may also be connected by wires or wireless to a handling system such as a robot to forward results based on the analyzed images or datasets to the handling system. The PLC may further be connected by wires or wireless to the first meat sensor.

The measuring bow may further comprise a user interface, by which a user may inform the processing unit of data related to at least one meat piece to be examine, such as type of meat piece, type of bones to examine, data relating to the animal type or race from where the meat piece is obtained, type of analysis to be performed and/or type of process to be performed after the analysis is performed.

The cameras to record red and blue light may be two cameras and may be located in a staggered arrangement when compared to the transport direction of meat pieces. Transversely to the transport direction the cameras may also be staggered and each of the cameras may be positioned to obtain optimal images of the meat piece being examined. Also along the direction of the transport direction the cameras may be staggered such as between 10 and 50 mm.

The first meat piece sensor may be connected to the at least one receiving sensor such as a camera and optionally also to the at least one first source for emitting electromagnetic waves and/or to the at least one second source for emitting electromagnetic waves such that when a meat piece passes the first meat piece sensor information is forwarded to the at least one receiving sensor initiating the function of the receiving sensors and optionally initiating the function of the sources for emitting electromagnetic waves. As soon as a meat piece conveyed by the conveyor belt is registered by the first meat piece sensor this sensor transmits a signal to the blue and red light source, and the blue and red camera (which together may be a single camera), which are then activated to emit light waves and record light waves. When the meat piece has passed the first meat piece sensor a signal is transmitted at least to the blue and red camera (which together may be a single camera), however, the light sources and camera(s) should not stop lighting and recording before the entire meat piece has been examined, a pre-determined time span may thus be determined before the camera(s) and optionally the light sources end recording data and lighting, respectively. Such a time span may be calculated due to the speed of the conveyor belt conveying the meat piece, and may be between e.g. 0.1 sec to e.g. 5 sec, preferably between 0.2 sec to 3 sec, more preferably between 0.3 to 2 sec, even more preferably between 0.1-1 sec or 0.1-1.5 sec.

The first meat piece sensor may be any kind of sensor capable of detecting the presence of a meat piece on a running conveyor belt. The first meat piece sensor may be a light beam e.g. positioned across the transport surface of the conveyor belt and when this light beam is interrupted it corresponds to the presence of a meat piece positioned on the conveyor belt. When the light beam in no longer interrupted this is interpreted such that the meat piece has passed the first meat piece sensor.

The measuring system may further comprise a second meat piece sensor for determining the presence of a meat piece being conveyed past a second position on the transport surface of the conveyor belt, wherein the first meat piece sensor may be located upstream of the second meat piece sensor according to the transport direction of meat pieces being conveyed on the conveyor belt and the second meat piece sensor may send information to an equipment such as a robot handling the meat piece.

The second meat piece sensor is preferably located along the conveyor belt at a position where the meat piece has passed the light sources and cameras for recording data used for determining presence and location of bones, and this recording of data has been performed. The second meat piece sensor may register the presence of a meat piece on the conveyor belt in the same way as the first meat piece sensor does. The second meat piece sensor may initiate a working tool such as a robot in a working zone along the conveyor belt. The second meat piece sensor may be located before or after such a working zone and may transmit information to a working tool such as a robot. The robot may operate a handling tool suitable to handle the meat piece, such a handling tool may be a bone removing tool e.g. a rib removing tool. The conveyor belt may be stopped when the second meat piece sensor register the presence of a meat piece and then the working tool such as a robot may handle the meat piece such as removing bones e.g. ribs. When the robot has ended its handling of the meat piece the conveyor belt may restart and convey the meat piece away from the handling zone. More preferably the handling of the meat piece is performed while the conveyor belt is running, hereby the second meat piece sensor transmits a signal to a robot when this sensor register the presence of a meat piece, the robot receives processed information such as of the positon, length and orientation of bones in the meat piece and the robot handles the meat piece such as loosen or removes the bones e.g. ribs.

An optical or ultrasonic height sensor may also be a part of the system such as integrated into a measuring bow. The height sensor is preferably facing downwards and being capable of measuring the height contour of the meat when a meat piece is transported under the height sensor. The height sensor can also be connected to the PLC by wires or wireless.

An optional encoder or resolver may also be a part of the system for measuring the conveyor speed and may be integrated into a measuring bow. The encoder or resolver may be connected to the PLC by wires or wireless. Alternatively, the conveyor speed can be measured once and configured as a parameter in the system.

The measuring system is described herein in combination with analyzing meat pieces which are conveyed such as by a conveyor belt. For situations where the meat pieces are not conveyed the measuring system may be the moving part. A measure bow may be moved above a non-moving meat piece and obtain data and perform the analysis as described herein. For such a system a measuring bow may comprise a moving system for moving the measure bow past the meat piece, the moving system may be located above the measure bow or along the area where the meat piece to be analyzed is located. Such moving systems for moving a bow are known by the skilled person.

The invention also relates to a method for determining the presence and/or positon of at least one bone in at least one meat piece while the meat piece is conveyed such as on a conveyer belt and where the method optionally further is for determining the length and/or orientation of the at least one bone, the method may comprise the steps of
  a. conveying at least one meat piece on a transport surface such as on a conveyor belt,
  b. directing electromagnetic waves towards a first surface of the at least one meat piece,
  c. directing electromagnetic waves towards a second surface of the at least one meat piece, where the second surface is not substantially parallel to the first surface,
  d. receiving electromagnetic waves of at least one pre-determined wave range and which are reflected from the first surface
  e. receiving electromagnetic waves of at least another pre-determined wave range and which are transmitted through the meat piece and emitted from the first surface of the meat piece and/or receiving electromagnetic waves of the at least another pre-determined wave range and which are emitted from a third surface of the meat piece, and
  f. processing the received electromagnetic waves to construct at least two images or datasets which may be superposed over each other such that one image or dataset is constructed which indicate the presence and/or position of at least one bone in the meat piece.

The method using the measuring system such as before using an industrial robot with the robot tool described herein for loosening bones may be described as:
  the electromagnetic waves directed towards a first surface of the at least one meat piece comprises at least light in the blue or green wave region such as light with wave lengths of between about 430-500 nm or 500-565 nm and
  the electromagnetic waves directed towards a second surface of the at least one meat piece comprises at least light in the red region including infrared region such as light with wave lengths of between about 620-1000 nm, and
  receiving light in the blue or green wave region which light is reflected from the first surface of the meat piece,
  receiving light in the red or infrared wave region which light is emitted from the first surface or from the third surface of the meat piece,
  processing the received light into at least two images or dataset and adding and/or subtracting data from the at least two image or dataset to indicate the presence and/or position of at least one bone in the meat piece.

The method can be further understood from the description of the function of the measuring system as well as from the example, from where features can be combined with the description of the method.

The use of the measuring system as described herein may be for determining the presence and/or positon of at least one bone in at least one meat piece. The use may be performed by the method as described herein. The use is preferably for determining the presence and/or positon of at least one rib in a belly piece but although described in respect of ribs should be understood as being suitable to determine the presence and/or position of other types of bones being located near the edge of a meat piece.

The measuring system as described herein above may be used for determining the presence and/or positon of at least one rib in a belly piece and loosening the ribs, such a system may be automatic and may comprise two individual subsystems located close to each other such as both located on the same conveyor belt, the subsystems may be:
  1. A measuring system, designed to determining the presence and/or positon and measure angle and length of each rib on a belly piece from e.g. a pig carcass,
  2. An industrial robot with a custom tool, such as a tool made specific for loosening of a rib on a belly piece.

The conveyor belt conveys the product first through the measuring system and then to the industrial robot. It is assumed that the product is not deformed during the transport between the two subsystems. The measuring system calculates coordinates as X and Y of the positions (length and width) of the bones based on the input from the cameras and the Z position (the height) from the height sensor. The calculations may include at least a start position of one or more bones present in the meat piece, an end position of the bones and the height within the meat piece of the start and end position of the bones resulting in determination of position, angle and length of bones within a meat piece. This information is communicated to an industrial robot capable of integrating the positions into an algorithm describing the working pattern of a tool mounted on the robot arm, and hereby a working pattern applicable for the meat piece to be handled is calculated. Based on the calculated working pattern the robot may handle the meat piece such as loosening or removing the bones from the meat piece.

The two subsystems are preferably connected communication wise through a form of physical and virtual protocol, e.g. TCP/IP on Ethernet, Canbus, Profibus, etc. The protocol is able to transport the measurements or processed data obtained in the measuring system from the measuring system to the robot.

A system for loosening or removing bones is further described herein and may be a part of the system with the two subsystems measuring system and industrial robot.

A calibration tool has been invented for calibrating the data obtained in the measuring system making it possible for the measuring system to locate the ribs in robot-space, such a calibration system may comprise the following:
  Calibration tool which in outer dimensions resembles the same area as the ribs of a meat product, and where
  the calibration tool has at least three fix points, located in the perimeter of the calibration tool, which can be located both optically by the measuring system, and tactile or near tactile by the robot, and
  the height of the calibration tool can be altered to represent the thinnest and thickest product and those in between.

The dimensions of the calibration tool may be altered to resemble the area or the bones in a meat piece which should be analyzed for determining the presence and/or position of bones.

The calibration process can be described as:
  The calibration tool is placed on the conveyor belt similar to a meat product when this meat product should be processed in the system described herein.
  When the calibration tool reaches the measuring system, it is scanned as a normal meat product, however the detection phase is different, in that it detects the at least three fix points.
  When the calibration tool reaches the second meat piece sensor located after the area of performing the scanning and in the robotics system, the conveyor belt stops.

The robot is manually jogged to each fix point of the calibration tool, so that the tool on the robot arm is placed relative to each point the same way it would be placed at a bone such as at a rib.

The position (X, Y, Z) of each fix point is read (manually or automatically) from the robot and inserted to the corresponding point found by the measuring system (manually or automatically).

The measuring system now has a three-point calibration which correlates image positions to robot positions, relative to the first and second meat piece sensors.

Detailed Description of the Figures

FIG. 1 illustrates a prior art pneumatic rib puller. The rib puller comprises a holding means (1) for holding or supporting the belly meat piece during the process of loosening or removing a rib, a movable pull bar (2) with a string at the end (3), a first handle (6) and a pneumatic system (7). When the string (3) is positioned around the tip of an exposed rib the pull bar (2) is draw towards the holding means (1) by activating the pneumatic system (7) and the string (3) while being dragged towards the holding means (1) will loosen the rib from the belly meat. To avoid rib cracks the abattoir worker with a hand presses the rib towards the belly meat while the string is being dragged towards the holding means (1).

Figure 2:
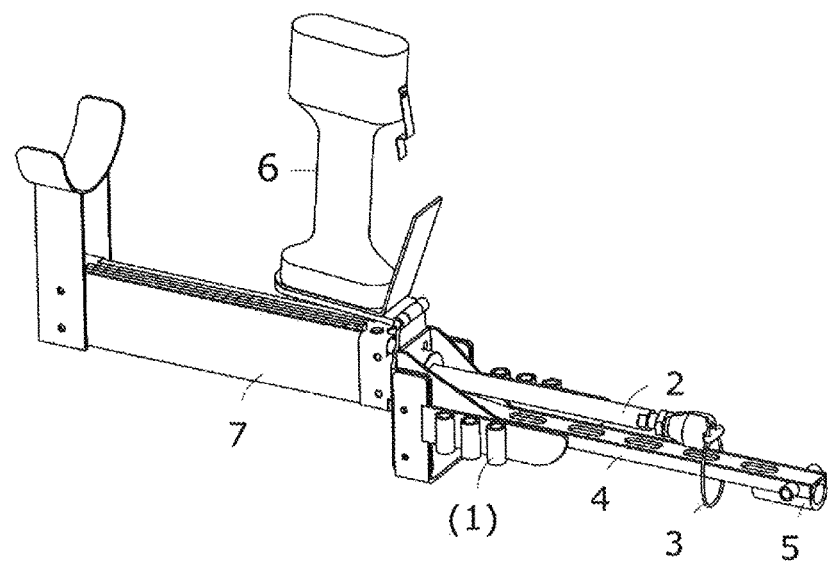
FIG. 2 illustrates a handheld pneumatic rib puller for loosening a single rib at a time according to the invention described herein.
Figure 3:
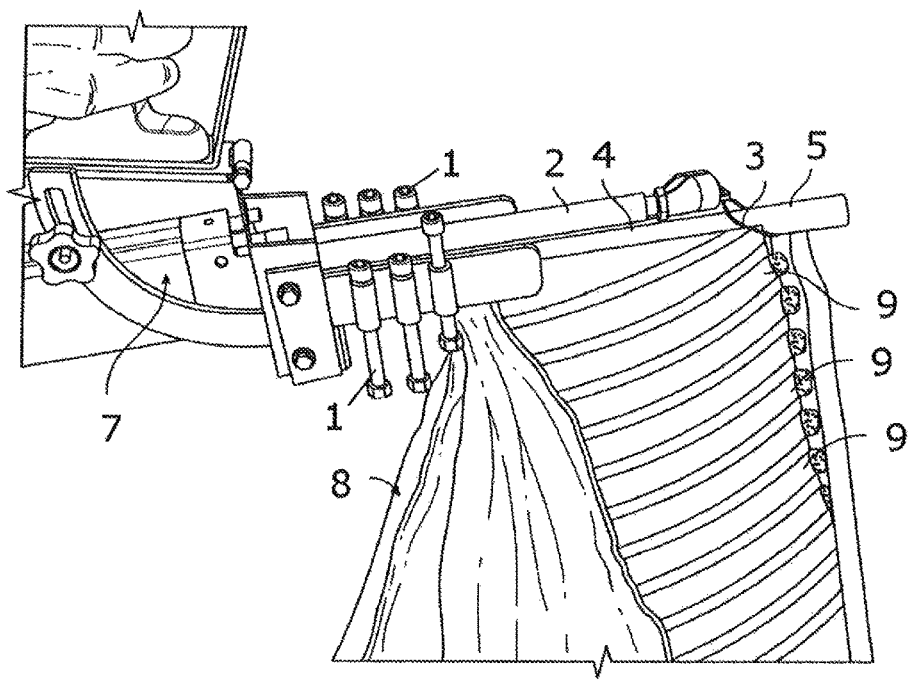
FIG. 3 illustrates a handheld rib puller located in a start position above a belly meat piece for loosening a single rib.

FIG. 2 illustrates a pneumatic rib puller according to the invention described herein. The rib puller comprises a holding means (1) for holding or supporting the belly meat piece during the process of loosening or removing a rib (the holding means is only partly illustrated in this figure. FIG. 3 illustrates an example of an entire holding means), a movable pull bar (2) with a string (3) at the end, a holding-down bar (4), loading means (5), a first handle (6) and a pneumatic system (7). The loading means (5) is hollow at least in the part facing the string (3) and the hollow part has a size in the form of opening area and length suitable to place the loading means (5) around the tip of an exposed rib. The rim of the loading means (5) in the part facing the string (3) may be sharp e.g. sharp as a knife, making it possible for it to cut into the belly meat when the loading means (5) is loaded on the tip of an exposed rib. When the rib puller is in function the string (3) and the loading means (5) are initially positioned around the tip of an exposed rib, then the pull bar (2) is draw towards the holding means (1) by activating the pneumatic system (7) and the string (3) while being dragged towards the holding means (1) will loosen the rib from the belly meat. The holding-down bar (4) will secure the rib is not lifted too much from the belly meat and/or is not cracking.

FIG. 3 illustrates the principle of locating a string around the cut end of a bone such as a cut end of a rib. The figure illustrates a hand-held rib puller located in a start position above a belly meat piece. The rib puller comprises similar features as described in respect of the rib puller illustrated in FIG. 2, and the function is similar to the description related to FIG. 2. The holding means (1) for holding the belly meat while loosening or removing a rib is illustrated with moveable elements on each side of the rib puller. These elements will adapt to the physical shape of the meat piece. Illustrated is exposed end of ribs (9) and a loading means (5) positioned right in front of a rib end.

FIG. 4 illustrates a rib puller for an industrial robot, where the rib puller is in the start position. The rib puller comprises a holding means (1) for holding or supporting the belly meat piece during the process of loosening a rib. The holding means (1) is shown in the form of two plates with pins where the plates are located on each side of a holding-down bar (4).

The holding means (1) are activated by a piston (24, FIG. 5) which pushes and holds the plates towards the meat. In this figure the piston are de-activated and the plates are in a non-holding position. The rib puller also comprises a movable pull bar (2) with a string (3) at the end, a holding-down bar (4), loading means (5), a motor such as a pneumatic system (7), an attachment device (10) for connecting the tool to an industrial robot, a piston (11) to move the tool away from the attachment device (10), piston guides (12) and a locking plate for shaft (13) securing the tool may stay in the position where the tool is pushed away from the attachment device (10). The loading means (5) is hollow forming a cavity when the holding-down bar (4) is moved in front of a cleaning plug (23) such that the loading means (5) encircles the rib end. The rim of the lower part of the loading means (5) may be sharp e.g. sharp as a knife, making it easy for it to cut into the belly meat when the loading means (5) is loaded on the tip of an exposed rib. When the rib puller is in function the string (3) and the loading means (5) are initially positioned around the tip of an exposed rib, then the pull bar (2) is pushed towards the holding means (1) by activating the motor such as a pneumatic system (7) and the end of the pull bar (2) with the string (3) continues pass the holding means (1) such that the string (3) while being dragged by the pull bar (2) will loosen the rib from the belly meat.

FIGS. 5 and 6 illustrate a rib puller for an industrial robot, where the rib puller is in the end position where the pull bar (2) is pushed along the holding down bar (4). The function of the tool is described further in respect of FIG. 4. FIGS. 5 and 6 also show how the holding means (1) are activated when a piston (24) has pushed the holding means (1) downward. FIG. 6 illustrates especially the holding means (1) with the pins and the cavity of the loading means (5) when the holding-down bar (4) is activated. The attachment device (10) for connecting the tool to an industrial robot is connected to a piston system which when activated pushes the entire tool away from the attachment device (10) and in this position a locking plate for shaft (13) secure the tool will stay in this position during loosening a rib.

Figure 7:
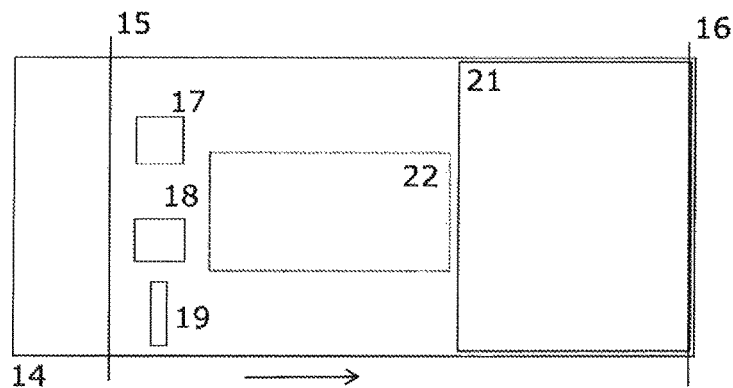
FIG. 7 is a schematic illustration with a top view of a measuring system and a working zone.

FIG. 7 is a schematic illustration with a top view of a measuring or scanning system and a working zone. A conveyor belt (14) conveys a meat piece (22). The meat piece (22) is shown at a position where the measuring or scanning has been finished and the meat piece (22) is under transport to a working zone (21). The running direction of the conveyor belt (14) is indicated by the arrow and the meat piece is conveyed from left to right on the conveyor belt (14) and when the meat piece starts to pass the first meat piece sensor (15) the measuring system starts lighting and recording lighting. The measuring system comprises red light (19), red camera (17), blue light (e.g. located beneath the blue camera) and blue camera (18). The measuring system stops lighting and recording lighting at a pre-determined time after the meat piece (22) has fully passed the first meat piece sensor (15). The recorded data is processed by a processor (not shown) and the information can be send to an automatic device such as an industrial robot (not shown) handling the meat piece in the working zone (21). An industrial robot may be activated when the second meat piece sensor (16) records the presence of the meat piece in the working zone (21).

Figure 8:
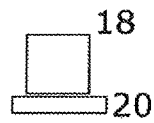
FIG. 8 is a schematic illustration with a side view of a measuring system and a working zone.
Figure 8:
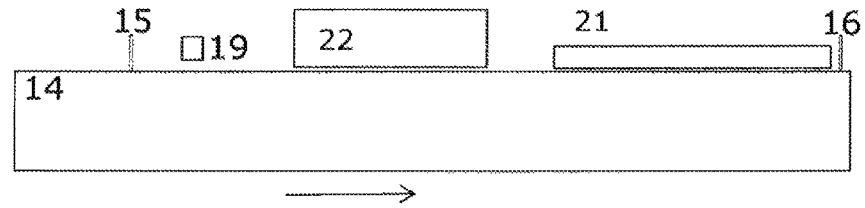

FIG. 8 is a schematic illustration with a side view of a measuring system and a working zone. The system is the same system as illustrated in FIG. 7. In this illustration it is shown how the blue light (20) can be located beneath the blue camera (18) and the red light (19) is located just above the conveyor belt (14). The first meat piece sensor (15) and the second meat piece sensor (16) are located just above the conveyor belt (14).

Figure 9:
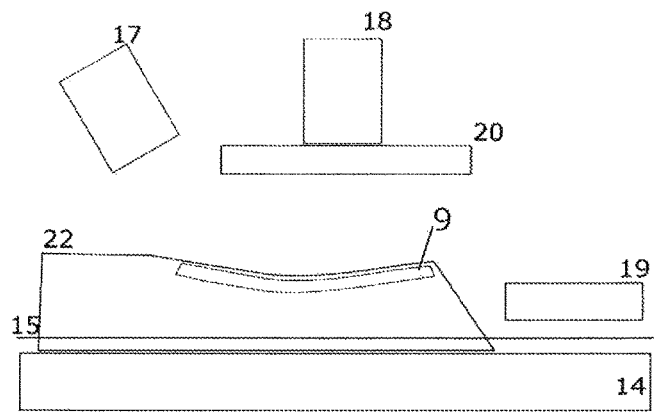
FIG. 9 is a schematic illustration with a transversal view of a measuring system.

FIG. 9 is a schematic illustration with a transversal view of a measuring system. The system is the same system as illustrated in FIG. 7 and FIG. 8. In this illustration it is shown how the blue light source (20) can be located beneath the blue camera (18) and the red light source (19) is located just above the conveyor belt (14) with the light being directed towards the meat piece (22) and the red camera (17) can be located away from the red light source (19) and angled to record red light from the meat piece (22). The exact location of the light sources and cameras are not illustrated. The red camera (17) should preferably be able to record red light from the area of the cut ribs (9) of the meat piece (22).

Figure 10:
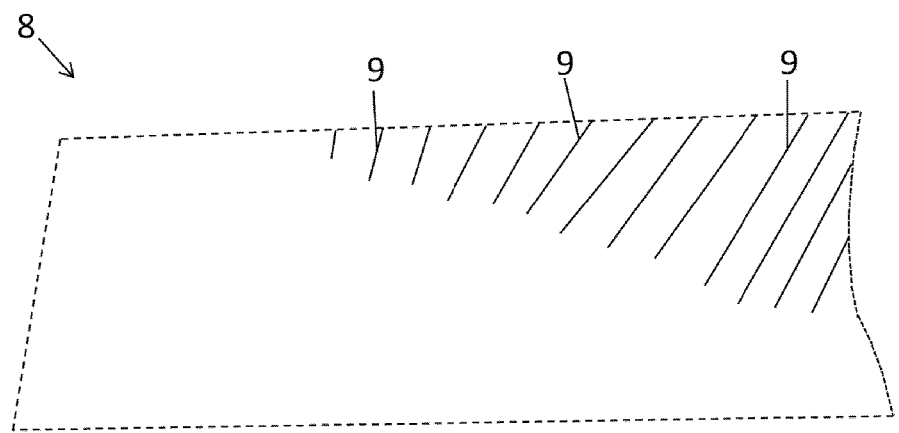
FIG. 10 is a schematic illustration of a belly piece with ribs where the skin is facing downward.
Figure 11:
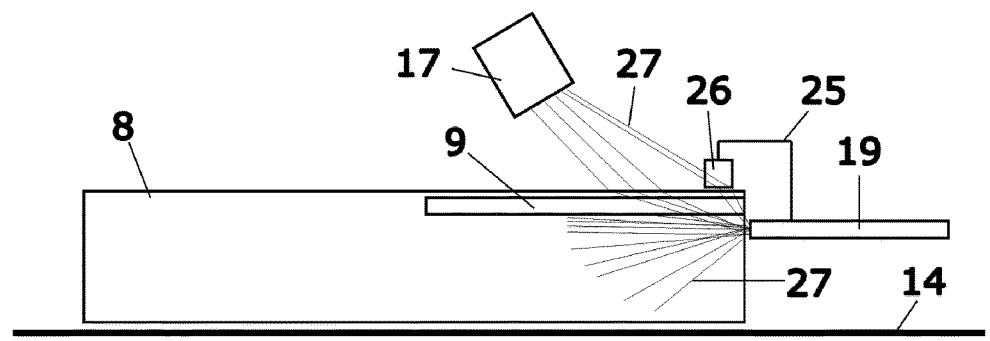

FIG. 10 is a schematic illustration of a belly piece (8) with ribs (9). Variation exists between animals due to e.g. distance between ribs, angling of ribs etc. The figure illustrates a pig belly piece (8) as it may be cut at an abattoir and thus illustrates ribs (9) of one individual animal. The dotted lines illustrate the contour of a cut belly piece (8). The belly piece (8) is cut with a total of 13 ribs (9) 11 of the ribs (9) have cut ends along the top line of the belly piece (8) and 2 odd ribs are cut differently when the right line of the belly piece was cut. The figure illustrates the different lengths of ribs (9) and the position of ribs (9) and hereby showing that different distances between ribs (9) occur. From the illustration different angling of the ribs (9) also appears. The distances between two adjacent ribs may be e.g. 30-50 in pork meat such as in pork meat obtained from pigs with a slaughter weight of about 60-110 kg. The angle of the ribs may be between 10-60° in respect of the cut exposing the cut bone ends.

EXAMPLES

Handheld Rib Puller

The device for loosening ribs as described herein has been tested by abattoir workers some of which were used to manage the prior art rib puller as shown in FIG. 1. The device was also tested by persons not used to handle the prior art rib pullers.

The rib puller was constructed as a pneumatic rib puller which was hand held by the abattoir workers. All ribs in the belly piece were loosened with the rib puller. It turned out that the rib puller was easy to use after a short training period and at the high speed necessary to pull ribs at a slaughter line, such as loosening ribs from about 525 bellies per hour with two to three abattoir workers each managing a rib puller.

Even the persons not used to handle a rib puller and who couldn't handle the prior art rib puller even after a short training period were capable of handling the rib puller with the holding-down bar and loading means after a short training period although not at the speed required at a slaughter line. It is thus easier to learn to manage the rib puller as described herein than the prior art rib puller shown in FIG. 1.

Rib Puller for an Industrial Robot

This example describes a setup of a measuring system as used for measuring the presence and position of ribs in pork chest pieces (belly pieces). The example further describes automatic removal of ribs from such pork belly pieces where the information obtained by the measuring system was processed and forwarded to a robot which removed the ribs from the belly piece.

Loosening of Single Ribs

The system consisted of two individual subsystems, both located on the same conveyor belt:

1. A measuring system, designed to locate and measure angle and length of each rib on a chest piece from a pig carcass, the system is illustrated in FIG. 7-9,
2. An industrial robot with a custom tool as illustrated in FIG. 4-6, made specific for loosening of a rib on the chest piece.

The conveyor belt conveyed the product (chest piece) first through the measuring system and then to the robot. The orientation of the products was such that the cut between the chest and the loin faced right in the transport direction i.e. with the cut ends of the ribs at the right side of the product determined according to the transport direction of the belly pieces. It is possible, without loss of generality, to mirror the system, so the cut faces the left side.

The two subsystems were connected communication wise.

Measuring System

The measuring system for determining the presence and position of ribs comprised the following:

1. A camera facing downwards, centered around the center of the product (the belly piece). The camera was run in a line scan mode, with each line being orthogonal to the transport direction. This camera was designated "the blue camera" and recorded light with blue wave lengths.
2. Blue light (LED), centered at the above camera's scan line and directed towards the rib part of the belly pieces such that the ribs were illuminated in the entire length.
3. A camera placed to the left (determined according to the transport direction of the belly pieces) of the blue camera, looking downwards in −30 degree angle (=30 degree counter clock wise). The camera was run in line scan mode, as with the blue camera. This camera is designated "the red camera" and recorded light with red wave lengths.
4. A powerful single red laser, placed horizontally on the right side (determined according to the transport direction of the belly pieces) of the product, lighting up the product just below the ends of the rib bones. The light was mounted on a ski (fixing ski) that was able to follow the contours of the ribs in such a way that the light was always just below the bones, independent of the height of the product and curvature of the bones.
5. An optical sensor (first meat piece sensor) placed a few centimeters before the scan lines of the cameras. The purpose of this sensor was to start and end the scanning of a product, and also to measure the length of the belly piece.
6. An optical or ultrasonic height sensor, facing downwards. The sensor measured the height contour of the meat.

The Measuring Process was as follows:

The product (belly piece) was transported on the conveyor belt and reached the first meat piece sensor, which initiated the scanning of the red and blue cameras, and the height sensor.

After the rear end of the product had left the first meat piece sensor and thus the scanning zone, the scanning stopped.

The line scans from each of the two cameras were stitched together to form two images. These images were analyzed, and the end of each rib, along with the length and angle were detected. The X, Y of the position (length and width) were calculated using the cameras, and the Z (the height) was calculated using the height sensor.

The measurements, position, angle and length of each rib were communicated to the robot before the first rib was loosened.

Detection Method

The red camera was used for detecting the start position (the cut end) of each rib, the blue camera was used for detecting the length and angle of each rib.

Red Camera

The red light easily penetrates the meat of the product, but not the bones. When line scanning the product while scanning from above and illuminating the side, the contour of the bones are detected as dark areas, whereas the area between the bones is clearly lit. The setup can be varied by switching position of camera and light source, the key point is that they are positioned roughly perpendicular to one another.

Blue Camera

The blue camera takes advantage of the fact that bone and fat are white and therefore reflects a lot of the blue light, while meat does not. Using blue light, the image from the blue camera have a high contrast between the bones and the meat between the bones. Optionally using the points located by the red camera, each rib bone is tracked to its endpoint and thereby obtaining the length and angle.

Robotics System

The robotic system for automatic removal of ribs from belly pieces comprised the following:
1. An industrial robot
2. A custom tool, able to loosen one rib at a time, while fixating the product so the other ribs maintained their position.
3. An optical sensor (second meat piece sensor), used for starting the process of loosening the ribs The process was as follows:

After measurement by the measuring system, the product continued to the second meat piece sensor, which triggered the activation of the industrial robot and the loosening of the ribs.

The robot looped through each position, angle and length, received from the measuring system. The process may be performed using conveyor tracking, but otherwise, the product as in this case stopped when it reached the second meat piece sensor.

The robot looped according to the information received from the measuring system:
  It moved to the start position of a rib, rotated the tool to the angle of the rib, and triggered the tool with the rib length.
  It then detached from the product, a few centimeters, before continuing to the next rib.

When all ribs were loosened, the robot returned to the initial position.

The rib puller for an industrial robot has thus been tested, where the measuring system determined the position, angle and length of the ribs in a belly piece from where the membrane (pleura) above the ribs was removed. The industrial robot handled the rib puller based on the information received from the measuring system and loosened all the ribs in a non-moving belly pieces in less than 25 sec and without breaking the ribs.

LIST OF REFERENCE SIGNS

1. Counter hold
2. Pull bar
3. String
4. Holding-down bar
5. Loading means
6. First handle
7. Motor such as a pneumatic system
8. Belly meat piece
9. Ribs
10. Attachment device for connecting the tool to an industrial robot
11. Piston
12. Piston guide
13. Locking plate for shaft
14. Conveyor belt
15. First meat piece sensor
16. Second meat piece sensor
17. Receiving sensor e.g. camera for recording red light 'red camera'
18. Receiving sensor e.g. camera for recording blue and/or green light 'blue camera'
19. Red light source
20. Blue or green light source
21. Working zone such as a working zone for removing bones
22. Meat piece/product
23. Cleaning plug

The invention claimed is:

1. A device for loosening at least one bone from a meat piece where at least one end of the at least one bone is exposed, said device comprising:
   at least one counter hold configured to support the device towards the meat piece; and
   at least one movable pull bar; and
   at least one string configured to loosen the at least one bone when being pulled along said at least one bone, where said string is fastened to said pull bar; and
   at least one longitudinal holding-down bar configured to hold down said at least one bone while loosening said at least one bone, where said holding-down bar is substantially parallel to said pull bar; and
   at least one loader configured to feed the string around an exposed portion of said at least one bone before loosening said at least one bone.

2. The device according to claim 1 wherein said at least one loader is connected to said holding-down bar and such that the string at least partly can surround the loader when the device is in a start position.

3. The device according to claim 1, wherein each of said at least one loader forms a cavity with said holding-down bar.

4. The device according claim 1, wherein said at least one counter hold comprises one or more of: a non-movable support, at least one movable support such as at least one vertically movable rod or element, or pins capable of holding said meat piece when said pins are pressed towards the meat piece.

5. The device according to claim 1, wherein said device is connected to a puller configured to activate the pull bar.

6. The device according to claim 1, wherein said device comprises a handle.

7. The device according to claim 1, wherein said device is a robot tool, said device further comprising:
   at least one attachment device for connecting the device to an industrial robot;
   wherein said at least one counter hold is configured to be pressed pressed towards said meat piece.

8. The device according to claim 7, further comprising a cleaning plug configured to remove one or more of: parts of meat, fat, tendon or membrane from said loader.

9. A bone loosening or bone removing system comprising:
a device for loosening at least one bone from a meat piece of a slaughtered animal where at least one end of said at least one bone is exposed, said device comprising:
   at least one counter hold configured to support the device towards the meat piece;
   at least one movable pull bar;
   at least one string configured to loosen said at least one bone when being pulled along said at least one bone, wherein said string is fastened to said pull bar;
   at least one longitudinal holding-down bar configured to hold down said at least one bone while loosening said at least one bone, wherein said holding-down bar is substantially parallel to said pull bar;
   at least one loader configured to feed said string around an exposed portion of said at least one bone before loosening said at least one bone; and
   an attachment device configured to connect the device to a robot arm, and
a robot comprising at least one working robot arm configured to connect to the device via the attachment device and manage the device in a process for loosening said at least one bone from said a meat piece of a slaughtered animal; and
at least one scanner configured to obtain scanning information when scanning at least one meat piece, wherein said scanner is configured to localizes one or more of: a presence of any bones located close to a surface of the at least one meat piece, a location of any bones located close to a surface of the at least one meat piece, or a size of any bones located close to the surface of each of the at least one meat piece, and
at least one processor configured to process said scanning information for said at least one meat piece and compute working paths for said robot arm including said device; and
a robot arm controller configured to manage said at least one robot arm based on working paths information received from said processor.

10. A method for at least partly loosening at least one bone from a meat piece of a slaughtered animal where at least one end of the at least one bone is exposed, said method comprising
   placing a device comprising at least one movable pull bar, at least one string fastened to said pull bar, and at least one longitudinal holding-down bar substantially parallel to said pull bar, and at least one loader configured to feed the string, such that said at least one holding-down bar is substantially parallel with said at least one bone or said at least one loader is in front of said at least one exposed bone end of said at least one bone, and with said string in front of the at least one exposed bone end,
   activating said pull bar whereby said string is pulled by said pull bar along said at least one bone and hereby loosening said at least one bone at least along part of a longitudinal direction of said at least one bone.

11. The method according to claim 10, further comprising:
   directing said loader over an outer part of said at least one exposed bone end.

12. The method according to claim 11, further comprising:
   returning said pull bar to its start position.

13. The method according to claim 10, further comprising:
   scanning said meat piece prior to placing said device to obtain information indicating a position of said at least one exposed bone end of said at least one bone.

14. The method according to claim 13, wherein said information further indicates a length of said at least one bone and an angle of said at least one bone with respect to a cut in the meat piece exposing the at least one bone ends.

15. The method according to claim 14, wherein said at least one bone comprises at least one rib.

* * * * *